United States Patent [19]

Harrison et al.

[11] Patent Number: 5,053,551

[45] Date of Patent: Oct. 1, 1991

[54] PROCESS FOR THE PRODUCTION OF ALDEHYDES BY HYDROFORMYLATION

[75] Inventors: George E. Harrison, Billericay; Alan J. Dennis, Acklam, both of England

[73] Assignee: Davy McKee (London) Limited, London, England

[21] Appl. No.: 278,437

[22] PCT Filed: Jun. 12, 1987

[86] PCT No.: PCT/GB87/00408

§ 371 Date: Nov. 21, 1988

§ 102(e) Date: Nov. 21, 1988

[87] PCT Pub. No.: WO88/00179

PCT Pub. Date: Jan. 14, 1988

[30] Foreign Application Priority Data

Jul. 1, 1986 [GB] United Kingdom ............... 8616038
Mar. 5, 1987 [GB] United Kingdom ............... 8705108
Mar. 17, 1987 [GB] United Kingdom ............... 8706265

[51] Int. Cl.$^5$ ............................................. C07C 45/50
[52] U.S. Cl. ................................. 568/454; 568/451; 568/492
[58] Field of Search ................... 568/454, 451, 492

[56] References Cited

U.S. PATENT DOCUMENTS

| | | | |
|---|---|---|---|
| 3,527,809 | 9/1970 | Pruett et al. | 568/454 |
| 4,148,830 | 4/1979 | Pruett et al. | 568/454 |
| 4,151,209 | 4/1979 | Paul et al. | 568/454 |
| 4,158,020 | 7/1979 | Stautzenberger et al. | 568/454 |
| 4,159,999 | 7/1979 | Stautzenberger et al. | 568/454 |
| 4,247,486 | 1/1981 | Brewster et al. | 568/454 |
| 4,260,828 | 4/1981 | Morrell et al. | 568/454 |
| 4,287,369 | 9/1981 | Harris et al. | 568/454 |
| 4,287,370 | 9/1981 | Harris et al. | 568/454 |
| 4,322,564 | 3/1982 | Tsunoda et al. | 568/454 |
| 4,329,511 | 5/1982 | Hackman et al. | 568/454 |
| 4,479,012 | 10/1984 | Fischer et al. | 568/454 |
| 4,567,306 | 1/1986 | Dennis et al. | |
| 4,577,043 | 3/1986 | Kalbfelt et al. | 568/492 |
| 4,678,857 | 7/1987 | Dureanleau | 568/492 |
| 4,792,636 | 12/1988 | Hensman et al. | 568/492 |

FOREIGN PATENT DOCUMENTS

| | | | |
|---|---|---|---|
| 028378 | 5/1981 | European Pat. Off. | 568/454 |
| 0996987 | 5/1983 | European Pat. Off. | 568/454 |
| 96986 | 12/1983 | European Pat. Off. | 568/454 |
| 96988 | 12/1983 | European Pat. Off. | 568/454 |
| 96987 | 11/1984 | European Pat. Off. | 568/454 |
| WO/8403697 | 9/1984 | PCT Int'l Appl. | 568/454 |
| 1440413 | 6/1976 | United Kingdom | 568/451 |
| 1458375 | 12/1976 | United Kingdom | 568/454 |
| 2055362 | 3/1981 | United Kingdom | 568/454 |
| 003697 | 9/1984 | World Int. Prop. O. | 568/454 |

Primary Examiner—Werren B. Lone
Attorney, Agent, or Firm—Bernard, Rothwell & Brown

[57] ABSTRACT

Continuous process for hydroformylation of olefins containing, typically, from 6 to 20 carbon atoms to produce the corresponding aldehydes. The rate of formation of high boiling aldehyde condensation products is minimized by use of a high boiling inert solvent whose boiling point, at the pressure prevailing in the product recovery zone, lies intermediate between that of the highest boiling aldehyde product produced in the hydroformylation reaction and that of the ligand, as well as by maintaining the concentration of product aldehyde at or below a predetermined minor amount. In this way the length of a production run can be significantly extended before it becomes necessary to shut down the plant due to accumulation of high boiling aldehyde condensation products.

19 Claims, 3 Drawing Sheets

PROCESS FOR THE PRODUCTION OF ALDEHYDES BY HYDROFORMYLATION

This invention relates to a continuous process for the production of aldehydes by hydroformylation of olefins.

Hydroformylation is a well known process in which an olefin, often a terminal olefin of the formula:

$$R.CH:CH_2,$$

where R represents a hydrogen atom or an optionally substituted hydrocarbon group, is reacted under elevated temperature and pressure conditions in the presence of a suitable catalyst with carbon monoxide and hydrogen to yield an aldehyde, according to the following equation:

$$R.CH:CH_2 + CO + H_2 = R.CH_2.CH_2.CHO.$$

Typically R represents a hydrogen atom or an alkyl radical.

The catalysts initially suggested were based on cobalt but these require use of high operating pressures and usually result in production of significantly high quantities of the corresponding alcohol of formula $R.CH_2.CH_2.CH_2OH$, as well as by-products such as acetals, esters, and the like. In addition, product recovery is complicated by the fact that the cobalt carbonyl catalysts are volatile and toxic, which means that the product stream from the hydroformylation zone has to be subjected to a decobalting step, a procedure which generally destroys the cobalt catalyst, before the decobalted product stream can be subjected to distillation or further treatment for recovery of aldehyde product. Hence, for economic operation, provision has to be made for recovering cobalt and for regenerating the cobalt catalyst therefrom. Ethylene gives rise to a single aldehyde hydroformylation product, i.e. propionaldehyde, but when propylene or a higher olefin is hydroformylated, the product stream always contains, besides the desired n-aldehyde, a proportion of the corresponding iso-aldehyde, which is formed according to the equation:

$$R.CH:CH_2 + CO + H_2 = R.CH(CHO).CH_3.$$

Typically the n-/iso-aldehyde product ratio from propylene and higher olefins, when using a cobalt hydroformylation catalyst, is of the order 4:1 or so.

A major advance in hydroformylation came with the advent of rhodium complex hydroformylation catalysts. These afforded great advantages, notably a non-volatile catalyst, a lower operating pressure, much reduced yields of alcohols and other by-products, and usually a significantly higher n-/iso- product aldehyde ratio. For further details of rhodium complex hydroformylation catalysts and conditions of operation therewith, the attention of the reader is drawn, for example, to U.S. Pat. No. 3,527,809. A description of a typical commercial plant employing such a catalyst will be found in the article: "Low-pressure OXO process yields a better product mix", Chemical Engineering, Dec. 5, 1977, pages 110 to 115.

The rhodium catalyst employed commercially in such a process generally comprises rhodium in complex combination with carbon monoxide and with a ligand, such as triphenylphosphine.

Usually the desired product of a hydroformylation reaction is the n-aldehyde, rather than the iso-aldehyde, for which there may be a limited commercial market; hence in many commercially operating hydroformylation plants the iso-aldehyde is burnt as a fuel since there is no ready market therefor. The use of a phosphine ligand, such as triphenylphosphine, has the advantage that high n-aldehyde/iso-aldehyde molar ratios can be obtained from terminal olefins. In some cases, however, the iso-aldehyde is the preferred product; for example, it has been proposed to produce isoprene from but-2-ene by hydroformylation to yield the iso-aldehyde, 2-methylbutanal, followed by dehydration by passage at elevated temperature over a suitable catalyst. When the desired product is the iso-aldehyde it has been proposed in EP-A-0096987 to use a rhodium complex hydroformylation catalyst and a phosphite ligand, such as triphenylphosphite. Alternatively it has been proposed in EP-A-0096988 to produce iso-aldehydes by hydroformylation of internal olefins using a rhodium complex hydroformylation catalyst and a cyclic phosphite ligand. Hydroformylation of alpha-olefins using a similar catalyst system to produce aldehyde mixtures whose n-/iso-aldehyde molar ratios approximate those obtained by using cobalt catalysts is described in EP-A-0096986.

Although the use of added solvents has been proposed on many occasions in the prior art, including U.S. Pat. No. 3,527,809, most commercially operating hydroformylation plants operate in so-called "natural process solvent", i.e. a mixture of aldehyde and aldehyde condensation products. The nature of such aldehyde condensation products is further discussed in U.S. Pat. No. 4,148,830.

At start up of a commercial plant product aldehyde is often used as the reaction solvent, this gradually being displaced by aldehyde condensation products until the "natural process solvent" has been generated.

It has been proposed to operate hydroformylation reaction using high boiling solvents, including ethylene glycol, propylene glycol and polyalkylene glycols such as diethylene glycol, triethylene glycol, dipropylene glycol and tripropylene glycol; the use of such solvents has been proposed in U.S. Pat. Nos. 4,158,020 and 4,159,999. Polyglycols, such as polyethylene glycol and polypropylene glycol, which have molecular weights of at least about 500, have been proposed as a solvent in U.S. Pat. No. 4,151,209; according to this last-mentioned proposal progressive deactivation of the catalyst, as well as loss of the ligand species through by-product formation, are reduced by continuously stripping the liquid reaction medium to a degree such that the content of high-boiling organophosphorous by-products therein is maintained at a low level such that the ratio of phosphorus contained in said high boiling by-products to phosphorus contained in the ligand present in the reaction medium does not exceed about 0.2. According to column 7, line 38 et seq:

". . . it is desirable to employ solvent species which are of extremely low volatility, in particular compounds (or mixtures of compounds) which are less volatile than the ligand species being employed in the hydrocarbonylation reaction."

Besides polyglycols (e.g. polyethylene glycol and polypropylene glycol), solvents recommended for use in the process of U.S. Pat. No. 4,151,209 include triphenylphosphine oxide and high-boiling esters of vapour pressure lower than that of the ligand being employed, either alone or in admixture with another solvent species, e.g. a polyglycol. A disadvantage of the use of glycols and polyglycols is that such materials can react with the aldehyde products to form cyclic or acyclic acetals. Hence glycols and polyglycols cannot be regarded as inert solvents.

U.S. Pat. No. 4,329,511 teaches a process in which a liquid which has a molecular weight of at least about 700 is used as a solvent for a rhodium complex hydroformylation catalyst. This specification teaches that: ". . . yet another parameter is of industrial significance in carrying out the product recovery at minimal cost and at optimal efficiency in, for example, the required rate of gas circulation necessary to recover the volatile products and simultaneously prevent build-up of the heavier reaction by-products. This additional parameter is the mole fraction of aldehyde in the liquid reaction medium contained in a hydroformylation reactor and, associated with the mole fraction, the molar concentration of product aldehyde in the liquid" (column 7, lines 40 to 51).

U.S. Pat. No. 4,329,511 further teaches that the hydroformylation reaction medium should contain at least about 50% of the high molecular weight diluent, computed on the product aldehyde-free basis (column 8, lines 38 to 43), whilst product aldehyde itself typically amounts to roughly 10% to 15% of the total reaction mixture (column 8, lines 66 to 68). The aldehyde content is controlled by controlling the intensity of the product stripping which is employed to remove the aldehyde from the reaction medium (column 9, line 35 et seq), it being recommended that stripping be so controlled as to maintain in the liquid reaction medium contained in the hydroformylation reactor an aldehyde content of about 1 to 2 gram moles per liter (column 9, lines 47 to 51).

Amongst methods of product recovery, U.S. Pat. No. 4,329,511 proposes withdrawal of a slip stream of liquid from the hydroformylation reactor, followed by distillation to recover a distillate comprising the aldehyde product, while leaving a distillation residue comprising the high molecular weight reaction solvent and catalyst, this residue then being returned to the hydroformylation reactor (column 7, lines 21 to 29). Alternatively the withdrawn slip stream can be subjected to simple evaporation (column 7, line 29 et seq of U.S. Pat. No. 4,329,511).

Although U.S. Pat. No. 4,329,511 proposes use of an alpha-olefinic hydrocarbons of 2 to about 20 carbon atoms, especially 2 to about 8 carbon atoms, difficulties arise due to considerations of vapour pressure at temperatures normally employed in the hydroformylation reaction systems, as discussed at column 4, line 15 et seq of U.S. Pat. No. 4,329,511. Hence the process of U.S. Pat. No. 4,329,511 is effectively restricted to use of olefinic hydrocarbons of 2 to about 6 carbon atoms, according to column 4, lines 21 and 22, ethylene and propylene being preferred.

It is well recognised in the prior art that, although it is possible to control to some extent the formation of aldehyde condensation by-products in the hydroformylation reaction medium, yet it is impossible to suppress entirely formation of such by-products. In the hydroformylation of low molecular weight olefins containing, for example, from 2 to about 5 carbon atoms, the resulting dimers and trimers are relatively low molecular weight compounds and their vapour pressure represents a minor, but significant, contribution to the total vapour pressure of the liquid medium. This means that, when operating with $C_2$ to $C_5$ olefins, the level of aldehyde condensation products in the liquid reaction medium can be controlled by using a sufficiently high gas recycle rate, as taught by U.S. Pat. No. 4,247,486. However, such measures cannot be used in practice when hydroformylating $C_6$ and higher olefins since the volatility of the aldehyde condensation by-products, specifically the "trimer III" and "trimer IV" type products (to adopt the nomenclature of U.S. Pat. No. 4,148,830) approaches that of triphenylphosphine and any attempt to control the level of aldehyde condensation by-products by the gas recycle process of U.S. Pat. No. 4,247,486 will tend to result in a concomitant loss of ligand from the hydroformylation medium. Moreover, in order to obtain a sufficiently high aldehyde condensation by-product vapour pressure, it is necessary to raise the reaction temperature to an unacceptably high level at which the risk of catalyst deactivation, by mechanisms such as rhodium cluster formation, and the rate of by-product formation become unacceptably high. If lower reactor temperatures are used, then the rate of gas recycle must be correspondingly increased which in turn leads to an unacceptably high capital cost for the gas recycle compressor and also unacceptably high operating costs, whilst the problem of potential ligand loss still remains.

For these reasons it is in practice necessary when operating with, for example, $C_6$ and higher olefins to recover product aldehyde from the hydroformylation reaction by distillation of, or evaporation from, a liquid product stream from the hydroformylation reactor.

Although the process of U.S. Pat. No. 4,329,511 recognises that it is beneficial to reduce the aldehyde concentration in the hydroformylation reaction medium so as to reduce the rate of aldehyde condensation product formation, yet the use of high boiling solvents leads in turn to further problems. Thus, for example, the use of high boiling solvents means that the temperature to which the hydroformylation medium is exposed in the distillation or evaporation step is increased with a consequent increase in the risk of catalyst deactivation as well as a corresponding increase in the rate of formation of aldehyde condensation by-products. Moreover, when operating the process continuously, removal of the inevitably formed aldehyde condensation by-products becomes problematic. In order to compensate for their formation it is necessary to purge some of the recirculating medium, which in turn means loss of rhodium catalyst and of ligand from the system. In view of the expense of rhodium and of the triphenylphosphine or other ligand, it is impractical to discard the purge stream and, as it is also expensive to store it and to replenish the reactor with fresh rhodium and ligand, it is accordingly necessary to include in the plant a catalyst and ligand recovery system for treatment of the purge stream for recovery of these valuable components.

The present invention seeks to provide an improved hydroformylation process for the production of $C_7$ and higher aldehydes from $C_6$ and higher olefins which can be operated continuously for extended periods of time and wherein the rate of formation of by-product aldehyde condensation by-products can be minimised. It further seeks to provide an improved process for effecting hydroformylation of $C_6$ and higher olefins in which adjustment of the volume of the circulating hydroformylation reaction medium, due to the inevitable formation of aldehyde condensation by-products, can be effected without loss of rhodium or ligand from the system.

According to the present invention there is provided a continuous process for the production of optionally substituted aldehydes containing at least 7 carbon atoms by hydroformylation of an optionally substituted olefin containing from 6 to about 20 carbon atoms, which process comprises:

providing a hydroformylation zone, a product recovery zone, and means for circulating liquid between said hydroformylation zone and said product recovery zone;

providing in said hydroformylation zone a substantially constant predetermined volume of a liquid hydroformylation medium containing uniformly distributed therein (a) a rhodium complex hydroformylation catalyst comprising rhodium in complex combination with carbon monoxide and with a ligand, (b) free ligand, (c) not more than a predetermined minor amount of at least one said optionally substituted aldehyde, and (d) an inert solvent that is less volatile than any optionally substituted aldehyde formed by the hydroformylation reaction but is more volatile than said ligand;

continuously supplying carbon monoxide and hydrogen to said hydroformylation zone;

continuously supplying said optionally substituted olefin to said hydroformylation zone;

maintaining said hydroformylation zone under hydroformylation conditions;

passing liquid hydroformylation medium to said product recovery zone;

maintaining said product recovery zone under vaporisation conditions selected to cause vaporisation of said at least one optionally substituted aldehyde and at least a minor amount of said solvent;

recovering from said product recovery zone (i) a vaporous stream containing a major amount of said at least one optionally substituted aldehyde and a minor amount of said solvent and (ii) a liquid stream containing said catalyst and said ligand;

continuously recycling said liquid stream to said hydroformylation zone;

controlling the vaporisation conditions in the product recovery zone so that the rate at which said solvent is recovered in said vaporous stream is at least equal to the rate of formation of aldehyde condensation by-products in said hydroformylation zone; and controlling the volume of liquid in said hydroformylation zone by supplying solvent thereto, if necessary, at a rate sufficient to maintain said substantially constant predetermined volume of liquid hydroformylation medium in said hydroformylation zone:

whereby the amount of said at least one optionally substituted aldehyde in said hydroformylation zone is maintained at or below said predetermined minor amount so as to minimise the rate of formation of aldehyde condensation by-products and whereby said solvent is gradually displaced from the hydroformylation zone by high boiling materials including aldehyde condensation by-products formed by self-condensation of said at least one optionally substituted aldehyde.

It will be appreciated by the skilled reader that the invention does not lie in the discovery of any new hydroformylation reaction system, insofar as the chemistry of such systems is concerned, but resides in use of an inert solvent having certain specific properties and in controlled vaporisation thereof in the product recovery step, and in controlling the volume of the hydroformylation reaction medium by supply, if necessary, of inert solvent thereto. In this way the concentration of aldehyde or aldehydes is kept as low as possible in the hydroformylation zone, which in turn results in a correspondingly low rate of formation of high boiling aldehyde condensation by-products which gradually displace the inert solvent as the reaction proceeds. The formation of high boiling aldehyde condensation by-products cannot be prevented entirely and these will inevitably accumulate in the liquid hydroformylation medium and will eventually cause problems in maintaining a constant volume of liquid hydroformylation medium in the hydroformylation zone, if the vaporiser temperature is maintained constant, or will eventually necessitate adoption of an unacceptable operating temperature and/or pressure of operation of the vaporiser simply in order to control the volume of the liquid hydroformylation medium. Hence eventually it will be necessary to shut down the plant and to recharge it with fresh liquid hydroformylation medium for one or other of these reasons. However, by selecting for use in the process of the invention a solvent which has a boiling point intermediate between that of the aldehyde product, or that of the highest boiling aldehyde product, and that of the ligand, the rate of formation of high boiling aldehyde condensation products can be minimised. Moreover, displacement of such solvent by high boiling aldehyde condensation by-products as these are formed can be accomplished without significant loss of ligand or catalyst from the circulating liquid and without exposing the catalyst to excessively high temperatures in the product recovery zone, since the temperature therein is limited by the boiling point of the solvent at the relevant operating pressure. By minimising in this way the rate of formation of aldehyde condensation by-products, which have, in general, boiling points that are similar to, or higher than, that of the ligand, it is possible to extend the length of production run, compared with conventional techniques in which the initial charge uses product aldehyde or aldehyde condensation by-products as solvent. Hence less frequent shutdowns of the plant are required when using the process of the invention than when using such conventional operating techniques.

The process can be used with optionally substituted olefins containing from about 6 to about 20 carbon atoms, preferably from about 8 to about 16 carbon atoms. Such compounds include not only olefins but also substituted olefins containing one or more substituents whose presence is not harmful to the hydroformylation catalyst under the selected hydroformylation conditions, for example ester or ether groups. The optionally substituted olefins may contain one or more alpha-olefinic groups of the formula —$CH:CH_2$ or $>C:CH_2$ and/or may contain one or more internal olefinic groups of the formula $>C:C<$. Illustrative optionally substituted olefins include 1-hexene, cis- and trans-2- and -3-hexene, 1-heptene, cis- and trans-2-, -3-, and -4-heptene, 1-octene, cis- and trans-2-, -3-, and -4-octene, 1-nonene, cis- and trans-4-nonene, 1-decene, cis- and trans-4-decene, 1-undecene, 1-dodecene, 1-tridecene, 1-tetradecene, 1-hexadecene, 1-octadecene, 2-, 3-, 4- and 5-methyl-1-hexene, 2-methyl-1-heptene, 2-methyl-2-heptene, 2-, 3-, and 4-methyl-1-pentene, 2-, methyl-2-pentene, cis- and trans-3-methyl-2-pentene, 2-methyl-1- and -2-heptene, allyl t-butyl ether, allyl propionate, allyl n-butyrate, allyl caproate, and the like.

In the hydroformylation of an olefin containing an alpha-olefinic group, such as 1-decene, the ligand is preferably a triarylphosphine, such as triphenylphosphine. However, when hydroformylating compounds containing one or more internal olefinic groups, such as trans-2-heptene, the ligand is preferably a triarylphosphite, such as triphenylphosphite, or a cyclic phosphite, such as one of the cyclic phosphites recommended in EP-A-0096988.

The liquid reaction medium contains a rhodium complex hydroformylation catalyst comprising rhodium in complex combination with carbon monoxide and with the ligand. Such catalysts can be preformed and then introduced into the reaction medium or the active catalyst species can be prepared in situ from a suitable catalyst precursor, such as (2,4-pentane dionato) dicarbonyl rhodium (I). Such methods for preparing reactive catalyst species are well known in the art.

The rhodium concentration in the reaction medium preferably ranges from about 20 ppm up to about 500 ppm or more, calculated as rhodium metal. However, in view of the expense of rhodium, the preferred rhodium concentration is from about 120 ppm up to about 300 ppm, calculated as rhodium metal.

The reaction medium contains excess ligand. Usually the ligand:rhodium molar ratio is at least about 2:1, preferably 3:1 or higher, up to about 100:1 or more. Preferably there is at least one mole of free ligand per mole of rhodium catalyst. Typically the concentration of ligand in the hydroformylation medium ranges from about 0.5% by volume, usually from at least about 1% by volume, up to about 50% by volume. For example, the ligand concentration may range from about 5% by volume to about 20% by volume when the ligand is a triaryl phosphine, such as triphenylphosphine, or is an alkyl diarylphosphine, such as hexyl diphenylphosphine, while somewhat lower ligand concentrations, for example from about 0.5% by volume up to about 10% by volume, may be preferred when a phosphite ligand, such as triphenylphosphite, or a cyclic phosphite ligand, such as one of those suggested for use in EP-B-0096988, is used.

The inert solvent can be any inert solvent that has a boiling point that is higher than any aldehyde formed by the hydroformylation reaction but lower than the boiling point of the ligand. Preferably the boiling point of the solvent at the pressure prevailing in the product recovery zone is at least about 10° C. higher than that of any aldehyde hydroformylation product at that pressure. Desirably it is also at least about 10° C. lower than the boiling point of the ligand at the pressure prevailing in the product recovery zone. The product recovery zone may be operated at atmospheric pressure when a $C_6$ olefin is used in the process of the invention. However, it is preferably operated at a sub-atmospheric pressure, particularly when a $C_8$ or higher olefin is used in the process of the invention.

The solvent is inert, that is to say it does not react with the aldehyde product or products or with any other component present in the liquid hydroformylation medium. Alcohols and other materials containing alcoholic hydroxyl groups, such as alkylene glycols, polyalkylene glycols, and mono-ethers and mono-esters thereof, are excluded from consideration since these materials may form high boiling cyclic or acyclic acetals with the aldehyde hydroformylation products and hence contribute to the problems associated with formation of high boiling by-products. As examples of suitable solvents there can be mentioned hydrocarbons, including paraffins and cycloparaffins, such as decane, dodecane, tetradecane, octadecane, ($C_1$- to $C_8$- alkyl)-decalins, ($C_6$-to $C_{12}$- alkyl)-cyclohexanes, and the like. Other suitable solvents include aromatic hydrocarbons, such as ($C_6$- to $C_{12}$- alkyl)-benzenes, ($C_1$- to $C_6$- alkyl)-naphthalenes, ($C_1$- to $C_6$- alkyl)-tetralins, o-terphenyl, m-terphenyl, diphenylmethane, and aryl naphthalenes, such as 1- or 2-phenylnaphthalene. Ethers are further examples of suitable inert solvents, including mixed aliphatic aromatic ethers. Examples are alkyl ethers of aromatic mono-, di- and polyhydroxy compounds, such as ($C_1$- to $C_{16}$- alkyl)-anisoles (e.g. 1-methoxy-4-ethylbenzene, 1-methoxy-3-n-decylbenzene, and the like), di-($C_1$- to $C_6$-alkoxy)-benzenes (e.g. 1,4-dimethoxy- and -diethoxybenzene and the like), ($C_1$- to $C_6$-alkyl)-dimethoxybenzenes (e.g. toluhydroquinone dimethyl ether and the like), ($C_6$- to $C_{12}$-alkoxy)-benzenes, and ($C_1$- to $C_{12}$-alkoxy)-naphthalenes. Aliphatic and cycloaliphatic ethers are further examples of ethers which can be used as solvent in the process of the present invention. Typical aliphatic ethers include $C_{12}$- to $C_{18}$- dialkyl ethers (e.g. di-n-hexyl ether, di-n-octyl ether, di-n-nonyl ether, n-butyl n-decyl ether, and the like), and triethylene glycol dimethyl ether. As examples of cycloaliphatic ethers there can be mentioned ($C_6$- to $C_{14}$-alkyl)-tetrahydrofurans, and ($C_6$- to $C_{14}$-alkyl)-1,4-dioxanes. Also contemplated for use as the inert solvent are ketones. Examples of suitable ketones include mono- and di-($C_1$- to $C_6$-alkyl) aryl ketones (e.g. acetophenone, 4-t-butylacetophenone, propiophenone, p-methylpropiophenone, n-hexyl phenyl ketone, and the like), ($C_1$- to $C_4$-alkyl) substituted diaryl ketones (e.g. 2-methylbenzophenone), $C_{10}$ to $C_{18}$ dialkyl ketones, and the like. As further examples of suitable solvents there can be mentioned materials derived from the product aldehydes, including dimethyl acetals, diethyl acetals, 2-alkyl-1,3-dioxolanes, and 2-alkyl-1,3-dioxanes derived from the product aldehyde or aldehydes or from an aldehyde of lower molecular weight than the product aldehyde or aldehydes. Also contemplated for use as inert solvent in the process of the invention are aldehyde condensation products formed in hydroformylation of $C_2$ to $C_5$ olefins, for example aldehyde condensation products of the type discussed in U.S. Pat. No. 4,148,830 formed by hydroformylation of propylene or of 1-butene. Mixtures of two or more solvents can be used.

It will be appreciated by the skilled reader that not every solvent in the above list can be used with every ligand and for hydroformylation of every $C_6$ or higher olefin. Generally speaking it will be necessary to select as a solvent a compound having a molecular weight which is, in general terms, intermediate between that of the product aldehyde or aldehydes and that of the ligand. In addition it will usually be preferred to select, if possible, a solvent whose boiling point is closer to that of the aldehyde product, or to that of the highest boiling aldehyde product, under the conditions prevailing in the product recovery zone than to that of the ligand. In this way the maximum temperature to which the catalyst-containing medium is exposed in the product recovery zone is kept as low as possible.

Boiling points of some typical aldehydes which can be produced by the process of the present invention are listed below:

| Aldehyde | Boiling point |
| --- | --- |
| n-heptanal | 59.6° C. at 30 mm Hg (0.040 bar) |
| n-octanal | 72° C. at 20 mm Hg (0.027 bar) |
| n-nonanal | 93.5° C. at 23 mm Hg (0.031 bar) |
| n-decanal | 81° C. at 7 mm Hg (0.009 bar) |
| n-undecanal | 117° C. at 18 mm Hg (0.023 bar) |
| n-dodecanal | 100° C. at 3.5 mm Hg (0.005 bar) |
| n-tridecanal | 156° C. at 17 mm Hg (0.017 bar) |
| n-tetradecanal | 166° C. at 24 mm Hg (0.032 bar) |

Boiling points of typical ligands are as follows:

| Ligand | Boiling point |
| --- | --- |
| Triphenylphosphine | 188° C. at 1 mm Hg (0.001 bar) |
| Triphenylphosphite | 200–201° C. at 5 mm Hg (0.007 bar) |
| Tri-o-cresylphosphite | 238° C. at 11 mm Hg (0.015 bar) |
| Tri-p-cresylphosphite | 250–255° C. at 10 mm Hg (0.013 bar) |

Boiling points of typical solvents are:

| Solvent | Boiling point |
| --- | --- |
| n-decane | 57.6° C. at 10 mm Hg (0.013 bar) |
| n-dodecane | 91.5° C. at 10 mm Hg (0.013 bar) |
| n-tetradecane | 121.9° C. at 10 mm Hg (0.013 bar) |
| n-octadecane | 173.5° C. at 20 mm Hg (0.027 bar) |
| heptylbenzene | 116° C. at 12 mm Hg (0.016 bar) |
| dodecylbezene | 185–188° C. at 15 mm Hg (0.020 bar) |
| 1-methylnaphthalene | 107.4° C. at 10 mm Hg (0.013 bar) |
| 2-methylnaphthalene | 104.7° C. at 10 mm Hg (0.013 bar) |
| 2-methyltetralin | 99–101° C. at 13 mm Hg (0.017 bar) |
| o-terphenyl | 160–170° C. at 2 mm Hg (0.003 bar) |
| diphenylmethane | 125.5° C. at 10 mm Hg (0.013 bar) |
| 1-phenylnaphthalene | 190° C. at 12 mm Hg (0.016 bar) |
| 2-phenylnaphthalene | 185–190° C. at 5 mm Hg (0.007 bar) |
| 1-methoxy-4-ethylbenzene | 83–84° C. at 16 mm Hg (0.021 bar) |
| di-n-octyl ether | 286–287° C. at 760 mm Hg (1.013 bar) |
| triethylene glycol dimethyl ether | 224–227° C. at 760 mm Hg (1.013 bar) |
| 1,4-dimethoxybenzene | 109° C. at 20 mm Hg (0.027 bar) |
| 1,4-diethoxybenzene | 246° C. at 760 mm Hg (1.013 bar) |
| hexyl phenyl ether | 130° C. at 22 mm Hg (0.029 bar) |
| 1-methoxynaphthalene | 135° C. at 10 mm Hg (0.013 bar) |
| 2-methoxynaphthalene | 138° C. at 10 mm Hg (0.013 bar) |
| 1-ethoxynaphthalene | 136–138° C. at 14 mm Hg (0.019 bar) |
| 2-ethoxynaphthalene | 148° C. at 10 mm Hg (0.013 bar) |
| 1-ethoxynaphthalene | 167° C. at 18 mm Hg (0.024 bar) |
| 2-propoxynaphthalene | 144° C. at 10 mm Hg (0.013 bar) |
| acetophenone | 79° C. at 10 mm Hg (0.013 bar) |
| 4-t-butylacetophenone | 136–138° C. at 20 mm Hg (0.027 bar) |
| propiophenone | 91.6° C. at 10 mm Hg (0.013 bar) |
| p-methylpropiophenone | 120° C. at 18 mm Hg (0.024 bar) |
| 2-methylbenzphenone | 128° C. at 12 mm Hg (0.016 bar) |

A mixture of aldehyde condensation products produced as by-products in the hydroformylation of propylene by the process of U.S. Pat. No. 3,527,809 is available from Union Carbide Corporation of Old Ridgebury Road, Danbury, Conn. 06817, United States of America, under the trade name "Filmer 351". This mixture is suitable for use in the process of the invention. It boils at 263.5° C. at 760 mm Hg (1.013 bar).

Although triphenylphosphine can be used as ligand when hydroformylating terminal olefins containing up to about 12 carbon atoms, it may be desirable to use a higher molecular weight ligand when hydroformylating higher olefins, for example a tri(alkyl- or alkoxyphenyl)-phosphine, such as tri-p-tolyl phosphine or tri-p-methoxyphenylphosphine, or a tri-halophenylphosphine, such as tri-(p-chlorophenyl)-phosphine, in place of triphenylphosphine. Other suitable phosphine ligands are mentioned, for example, in U.S. Pat. No. 3,527,809. Similarly, when using a phosphite ligand in the process of EP-A-0096987, another of the phosphites mentioned therein and having a higher molecular weight than triphenylphosphite may be substituted for triphenylphosphite in the process of the present invention. Similarly, it is possible to use in the process of the present invention any of the cyclic phosphites mentioned in EP-A-0096988 or EP-A-0096986 in place of the preferred ligand disclosed therein, i.e. 4-ethyl-2,6,7-trioxa-bicyclo-[2,2,2]-octane.

In operation of the process of the invention it will usually be desirable to select a ligand which has, at the pressure prevailing in the product recovery zone, a boiling point at least 20° C. higher than any product aldehyde produced in the hydroformylation zone and to select an inert solvent that has, at the same pressure, a boiling point that is at least 10° C. higher than that of any product aldehyde but lower than that of the chosen ligand.

In operation of the process of the invention, the liquid hydroformylation medium will contain, in addition to the rhodium complex hydroformylation catalyst, free ligand and inert solvent, also unreacted olefin and product aldehyde or aldehydes, besides by-products, including hydrogenation products (e.g. alkanes) and "heavies", including aldehyde condensation by-products formed by condensation of the product aldehyde or aldehydes, for example "trimer III" and "trimer IV" type products of the kind disclosed in U.S. Pat. No. 4,148,830.

In the process of the invention the vaporous stream recovered from the product recovery zone contains, in addition to the desired optionally substituted aldehyde or aldehydes and any materials with lower boiling points than the product aldehyde or aldehydes, such as unreacted starting olefin and minor amounts of any hydrogenation by-product thereof, also a minor amount of inert solvent. Such solvent is usually recovered in a downstream solvent recovery zone, which may be located either immediately downstream from the product recovery zone or downstream from a subsequent process step, such as downstream from a hydrogenation step or downstream from aldolisation, dehydration, and hydrogenation steps, depending upon whether the desired end product is an alcohol having the same number of carbon atoms as the product aldehyde or aldehydes or an alcohol having twice as many carbon atoms as the product aldehyde or aldehydes. When using a ketone solvent it is preferable to locate the solvent recovery zone immediately downstream from the product recovery zone since the ketone will otherwise undergo at least partial hydrogenation in passage through an aldehyde hydrogenation zone and hence yield a secondary alcohol; in other words the ketone will be converted into a non-inert solvent.

It is possible so to operate the process that the rate of removal of solvent in the vaporous stream from the product recovery zone is substantially equal to the rate of formation of aldehyde condensation products. In this case no make up solvent is required in order to maintain the predetermined volume of liquid hydroformylation medium in the hydroformylation zone.

Alternatively it is possible to operate the process such that the rate of removal of inert solvent in the vaporous stream from the product recovery zone exceeds the rate of formation of aldehyde condensation by-products. In this case the volume of liquid hydroformylation medium can be maintained constant in the hydroformylation zone by supplying fresh solvent or solvent recovered in the downstream solvent recovery zone as make up solvent.

We have found that, under hydroformylation conditions, the formation of aldehyde condensation by-products is approximately second order with respect to aldehyde concentration. Hence, in order to maintain the rate of formation of aldehyde condensation by-products as low as possible, it will usually be preferred to select a rate of recovery of the liquid hydroformylation medium from the hydroformylation zone and to adjust the rate of recycle of catalyst containing solution and, if necessary, the rate of supply of solvent to the hydroformylation zone so as to maintain in the hydroformylation zone a product aldehyde concentration of not more than about 2 gram moles per liter of reaction medium, typically from about 1 to about 2 gram moles of aldehyde per liter of reaction medium.

The hydroformylation zone may comprise a single reactor. Alternatively it may comprise two or more reactors connected, for example, in series.

The hydroformylation zone is operated under hydroformylation conditions, such hydroformylation conditions being selected in dependence upon the nature of the olefin, the ligand, the rhodium concentration and other design factors, as will be immediately apparent to the man skilled in the art. For details of typical hydroformylation reaction conditions reference should be made to U.S. Pat. No. 3,527,809, 4,148,830, 4,247,486, EP-A-0096986, EP-A-0096987, EP-A-0096988 and other patent specifications describing rhodium catalysed hydroformylation reactions. Generally speaking such conditions include use of a temperature in the range of from about 40° C. to about 160° C. and a pressure in the range of from about 1 bar absolute to about 100 bar absolute.

The product recovery zone is preferably operated under reduced pressure as a distillation zone or as an evaporation zone. It is preferably operated at a sub-atmospheric pressure in order to limit as far as possible the exposure of catalyst and of aldehyde to elevated temperatures in excess of the temperature in the hydroformylation zone. Typical operating conditions in the product recovery zone include use of temperatures in the range of from about 60° C. to about 200° C., pressures in the range of from about 0.0001 bar to about 0.5 bar, and residence times which are as short as possible, preferably in the range of from about 2 seconds to about 5 minutes, for example in the range of from about 5 seconds to about 2 minutes. Preferably the product recovery zone is operated at a temperature which is no higher than about 160° C. and even more preferably no higher than about 150° C. Due precautions must be taken in the product recovery zone to obviate loss of catalyst solution components with the hydroformylation product and inert diluent vapours due to entrainment of droplets in the vaporous stream. The product recovery zone can comprise a distillation column but preferably comprises a wiped film or falling film evaporator, since such evaporators enable residence times in the product recovery zone to be minimised.

The solvent recovery zone may follow immediately after the product recovery zone. In this case the solvent recovery zone can comprise a fractionation zone, from which the product aldehydes are recovered overhead, together with unreacted olefin or olefins and hydrogenation by-products, whilst the solvent appears as a bottom product therefrom.

It is also feasible to subject the mixture of aldehyde and solvent to further processing steps, for example, to hydrogenation or to aldolisation, dehydration and hydrogenation, so as to produce the corresponding alcohol. In this case the solvent recovery zone can follow such further processing steps. Distillation is a suitable method of solvent recovery.

Figure 1:
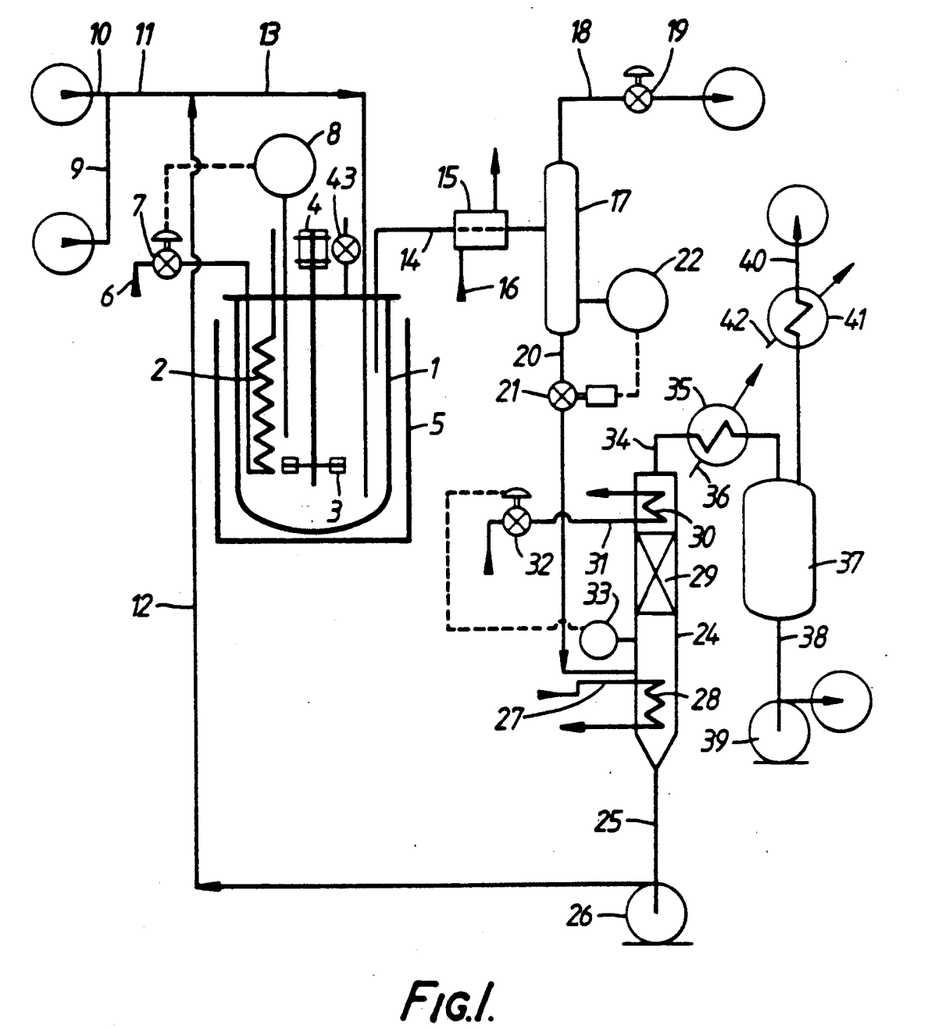

FIG. 1 of the drawings is a flow diagram of a laboratory scale apparatus for studying continuous hydroformylation of olefins using a rhodium complex hydroformylation catalyst which can be used for operation of the process of the invention. This includes a 2-liter stainless autoclave 1 fitted with an internal cooling coil 2 and with a magnetically coupled stirrer 3 which is arranged to be driven by a motor 4. The stirrer 3 has a hollow shaft and is designed so as to induce gas down its hollow shaft from the head space above the liquid level within autoclave 1 and to disperse such gas into the liquid charge within autoclave 1. Autoclave 1 and its contents can be heated by means of a thermostatically controlled oil bath 5, whose temperature is controlled to be approximately 2° C. above the temperature desired in autoclave 1. Fine control of the temperature of the liquid charge in autoclave 1 is achieved by allowing cooling water, supplied in line 6, to flow through cooling coil 2 by opening valve 7 which is controlled by a temperature controller 8.

Liquid 1-decene is supplied to reactor 1 in line 9 and a $CO/H_2$ mixture is fed to the apparatus in line 10. The olefin and the mixture of CO and hydrogen supplied to the apparatus is previously subjected to rigorous purification for the removal therefrom of sulphurous and halogenated impurities which are known to act as catalyst poisons for rhodium complex hydroformylation catalysts. The resulting mixture of olefin, CO and hydrogen passes on in line 11, is admixed with catalyst recycle solution in line 12, and then flows into autoclave 1 by way of line 13. Liquid reaction medium is recovered from autoclave 1 in line 14 and is cooled in cooler 15, which is supplied with cooling water in line 16. The position of the lower end of line 14 within autoclave 1 enables the volume of liquid in autoclave 1 to be set at a predetermined level during operation. The cooled reaction medium in line 16 then enters vapour/liquid separator 17 in which some of the dissolved gases flash off and are recovered in line 18 to exit the apparatus via pressure control valve 19. The substantially degassed liquid phase then passes in line 20 via pressure reduction valve 21, which is under the control of level controller 22, to line 23 and thence to evaporator 24 which is operated under sub-atmospheric pressure.

Product aldehydes are vaporised in evaporator 24, together with a proportion of any other component present whose boiling point is lower than that of the ligand, whilst rhodium catalyst, ligand and aldehyde condensation by-products, are recovered in line 25 for recycle to line 12 with the aid of pump 26. If desired the bottom of evaporator 24 can be filled with glass beads, or a similar inert filling, so as to reduce the volume of liquid therein and hence reduce the residence time of the liquid at elevated temperature in evaporator 24.

Hot oil is supplied in line 27 at 150° C. and is circulated through heating coil 28 at a rate such that the level of liquid in the bottom of evaporator 24 tends to fall. A vaporous mixture containing product $C_{11}$ aldehydes and other "light" materials present, such as unreacted 1-decene, isomerised $C_{10}$ internal olefins, such as cis- and trans-2-decane, and hydrogenation produce (i.e. n-decane) passes upwards through packing 29 and is partially condensed by evaporator reflux condenser 30. The reflux stream induced by condenser 30 flowing down over packing 29 ensures that substantially all materials with boiling points higher than the $C_{11}$ aldehyde products, including the ligand, are condensed and returned to the bottom of evaporator 24 and that only an amount of material with a boiling point higher than the $C_{11}$ aldehyde products which corresponds to the rate of formation of aldehyde condensation by-products passes overhead in the vaporous stream in line 34 with the $C_{11}$ aldehyde products. Condenser 30 is supplied with cooling water in line 31 under the control of a valve 32 which is in turn controlled by a level controller 33. Uncondensed vapours are recovered overhead from evaporator 24 in line 34 and pass through condenser 35 which is supplied with cooling water in line 36. The resulting condensate is collected in a graduated product vessel 37, from which liquid condensate is removed for analysis from time to time in line 38 by means of pump 39. Line 40 is connected to a vacuum pump (not shown) by means of which evaporator 24 and product vessel 37 are maintained under reduced pressure. Condenser 41, which is supplied with chilled cooling water in line 42, serves to minimise loss of condensible materials in line 40.

At start up of the apparatus 1.15 liters of hydroformylation medium containing 10% w/w triphenylphosphine and 250 ppm w/w rhodium metal in the form of hydridocarbonyl tris-(triphenylphosphine) rhodium (I), i.e. $HRh(CO)(PPh_3)_3$, or of a catalyst precursor, such as (2,4-pentane dionato) dicarbonyl rhodium (I), is charged to autoclave 1 which is then purged of air through vent valve 43 by repeated pressurisation and then depressurisation with nitrogen, followed by passage of nitrogen through lines 10, 11, 13, 14 and 18, valve 19 being opened for this purpose. During this operation approximately 150 ml of liquid is transferred to vapour/liquid separator 17. Hence the "dynamic volume" of liquid in the autoclave 1 under operational conditions is approximately 1 liter.

Level controller 22 is then actuated so that liquid begings to accumulate in the bottom of evaporator 24. Recycle pump 26 is then started to return liquid to the autoclave 1 via lines 25 and 12. At the same time the vacuum pump is started so as to evacuate product vessel 37 and evaporator 24 to a pressure of 10 mm Hg (0.0133 bar). When the desired operating pressure has been achieved in evaporator 24 and product vessel 39, pump 26 is adjusted until its flow rate is 400 ml/hour. Liquid is allowed to circulate while 50 liters hour of nitrogen is supplied by way of line 10 to autoclave 1, thereby lifting liquid via line 14 to liquid/vapour separator 17. Next the pressure control valve 19 is adjusted to give a reactor pressure of 110 psig (8.58 bar) and autoclave 1 is heated to 80° C. using the external oil bath 5. The gas supply in line 10 is then changed to 50 liters hour of a mixture of carbon monoxide and hydrogen, whilst 400 ml/hour of 1-decene is supplied through line 9.

The gas supply is increased progressively to approximately 84 liters/hour so that about 5 to 6 liters/hour of gas is vented through line 18. The temperature of oil bath 5 is then held at about 82° C. while water is supplied through cooling coil 2 to maintain the temperature in autoclave 1, as detected by temperature controller 8, at 80° C.

Hot oil is circulated at 153° C. through line 27 at a rate such that the level in evaporator 24 tends to fall by reason of the material boiling. The condensate collecting in product vessel 37 contains the net "make" of $C_{11}$ "Oxo"-aldehydes, by-product paraffin and internal olefin. Packing 29 serves to prevent any triphenylphosphine, entrained solution droplets and heavy by-product materials reaching product vessel 37.

During the initial start-up period the ratio of hydrogen and carbon monoxide in the feed gas supplied in line 10 is adjusted slightly so that the $H_2:CO$ molar ratio in line 18 is 3:1. After about 10 hours operation the system is found to operate in a steady manner.

The invention is further illustrated in the following Examples in which the apparatus of FIG. 1 is used.

COMPARATIVE EXAMPLE A

The liquid charged to autoclave 1 is a solution of 10% w/w of triphenylphosphine in 1-undecanal containing 250 ppm w/w of dissolved rhodium, the rhodium being added in the form of $HRh(CO)(PPh_3)_3$. After steady state operation conditions are achieved the reactor is operated for 30 days under the following conditions:

| | |
|---|---|
| Reactor Temperature | 81° C. ± 2° C. |
| ppm w/w rhodium | 248 ± 5 |
| % w/w triphenylphosphine in reactor | 10.1 ± 0.6 |
| Hydrogen partial pressure in reactor | 90 psi ± 2 (6.21 bar ± 0.14) |
| Carbon monoxide partial pressure | 30 psi ± 1.2 (2.07 bar ± 0.08) |
| Residence time in evaporator 24 | 30 seconds |

Under these conditions the following results are obtained:

| | |
|---|---|
| % olefin converted | 84.0 ± 2 |
| % n-aldehyde selectivity in product | 85.5 ± 1 |
| % iso-aldehyde selectivity in product | 8.2 ± 0.3 |
| % (decane + internal decenes) | 6.3 ± 0.2 |

Analysis of the reactor solution by gas chromatography shows that "heavies", i.e. aldehyde condensation by-products, accumulate in the reactor solution in the manner set out in Table 1 below. The method of analysis uses a Pye Unicam PU 4500 capillary column chromatograph fitted with a flame ionisation detector and using helium as the carrier gas. The column is a 25 meter SE54 capillary column with an inside diameter of 0.32 mm and a film thickness of 0.23 $\mu m$. With an inlet splitter ratio of 100/1 and an inlet carrier gas pressure of about 2.1 bar absolute 0.5 $\mu l$ samples are subjected to temperature programming as follows: 5 minutes isothermal operation at 150° C., followed by an increase in temperature to 300° C. at 20° C./minute, followed by a final 10 minutes isothermal stage at 300° C.

TABLE 1

| Days of operation | % w/v "heavies" in reactor solution |
|---|---|
| 5 | 2.81 |
| 10 | 5.50 |
| 15 | 7.91 |
| 20 | 10.10 |
| 25 | 12.32 |
| 30 | 14.42 |

By extrapolation from this data it is possible to calculate that the "heavies" concentration will reach 40% by volume in approximately 133 days, at which stage it will probably become expedient to shut the reactor down because it will have become difficult or impossible to control the volume of liquid in the apparatus.

EXAMPLE 1

The procedure of Comparative Example A is repeated except that the 1-undecanal used as solvent in the initial liquid charge is replaced by a 60:40 undecanal:-diphenyl ether v/v mixture. The reaction conditions are as set out above in the Comparative Example. In this case a minor amount of diphenyl ether passes overhead in line 34, at a rate corresponding to the rate of formation of aldehyde condensation by-products, and collected in product vessel 37. The build-up of "heavies" in the reaction medium is monitored in a similar manner to that used in Comparative Example A with the results set out below in Table 2.

TABLE 2

| Days of operation | % w/v "heavies" in reactor solution |
|---|---|
| 5 | 0.70 |
| 10 | 1.45 |
| 15 | 2.17 |
| 20 | 2.88 |
| 25 | 3.61 |
| 30 | 4.36 |

From these figures it is possible to calculate by extrapolation that it will take approximately 270 days before the "heavies" level reaches 40% v/v of the reactor solution and it becomes expedient to shut down the reactor because all of the diphenyl ether will have been displaced from the reaction system and it will become increasingly difficult to control the volume of liquid in the apparatus. In addition, the temperature of the liquid in the bottom of evaporator 24 will tend to increase after all the diphenyl ether has been displaced, thereby increasing the risk of catalyst deactivation and also the rate of formation of aldehyde condensation by-products.

It will be readily apparent to those skilled in the art from these results that, by using an inert solvent in accordance with the teachings of the invention it is possible to prolong substantially the length of a hydroformylation run, thus extending the interval between successive shutdowns of the plant and increasing the annual production capacity of the plant.

COMPARATIVE EXAMPLE B

The apparatus used in this experiment was constructed as illustrated diagrammatically in FIG. 1 except that the volume of autoclave 1 was 300 cc which was charged at start up with 175 ml of a solution containing 10% w/v triphenylphosphine in n-nonanal containing 200 ppm w/w rhodium added as $HRh(CO)(PPh_3)_3$. Instead of n-decene, however, the olefin was liquid 1-octene; this was fed to autoclave 1 at an initial liquid feed rate of 58 ml/hr. The feed gas was a mixture of $H_2$, CO and $N_2$. Under steady state conditions the reactor temperature was held at 120° C., with a total pressure of 195 psia (13.44 bar). The hydrogen partial pressure was 60 psia (4.13 bar), whilst that of carbon monoxide was 15 psia (1.03 bar) and that of nitrogen and the organic components was 120 psia (8.27 bar). The liquid recycle rate in line 12 was 90 ml/hr, whilst the temperature in evaporator 24 was maintained by supplying hot oil at a temperature of from about 110° C. to about 120° C. in line 27. The pressure in evaporator 24 was 10 mm Hg (0.0133 bar). Using an analysis technique similar to that described above in Comparative Example A, the concentrations of aldehyde (i.e. n-nonanal) and of "heavies" (i.e. mainly $C_{18}$-dimers and $C_{27}$-trimers) were determined from time to time after steady state operating conditions had been achieved. The results are plotted in FIG. 2. After 47 hours it was necessary to reduce the 1-octene feed rate to 30 ml/hr in order to maintain the temperature in evaporator 24 below 120° C.

Figure 2:
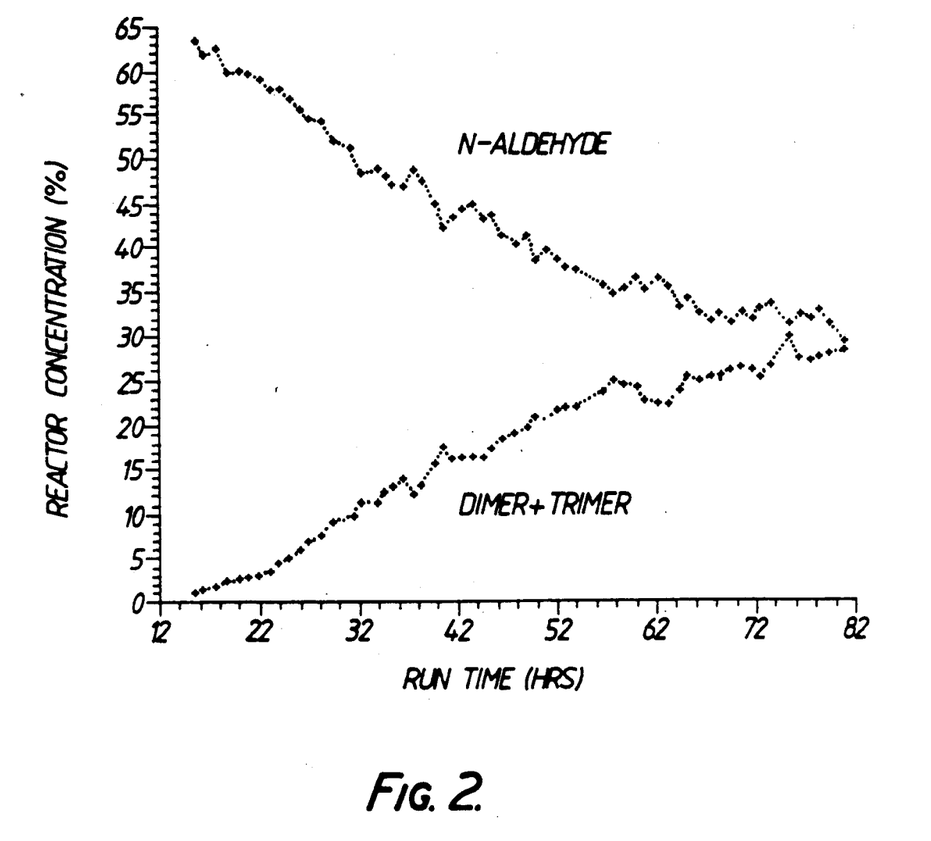

It will be noted from FIG. 2 that, although the rate of "heavies" formation was initially quite low, this rate increased quite rapidly after about 24 hours of operation to a maximum rate. Moreover it appeared that the formation of $C_{18}$ and higher "heavies" results from an approximately second order reaction.

Due to the rapid increase of the "heavies" concentration, it would soon have been necessary, probably no more than about 24 hours later, to shut down the reaction system because it would have become necessary to raise the temperature of evaporator 24 appreciably above 120° C., with a consequent increased risk of thermal deactivation of the rhodium complex catalyst, in order to evaporate the $C_{18}$ and higher "heavies" and to prevent them from flooding the system.

It will be appreciated by the skilled reader that the operating conditions used in Comparative Example B were selected so as to provide an accelerated rate of "heavies" formation such that the experiment could be completed within a reasonable time. In practice, operating conditions for a commercial plant could be somewhat less severe; in particular, an operating temperature appreciably lower than 120° C. (e.g. about 80° C. to about 105° C.) could be used, which would result in a correspondingly lower rate of "heavies" formation.

EXAMPLE 2

Using the same apparatus as was used in Comparative Example B, autoclave 1 was charged with a rhodium-free solution containing 10% w/v triphenylphosphine dissolved in a 50/50 v/v mixture of Filmer 351 and n-nonanal. (Filmer 351 is a mixture of aldehyde condensation products of the type discussed in U.S. Pat. No. 4,148,830, obtained as a by-product of the hydroformylation of propylene; it is mainly a mixture of $C_{12}$ "trimer III" and "trimer IV" type products and has a boiling point at 10 mm Hg (0.0133 bar) of approximately 140° C. "Filmer" is a trade name of Union Carbide Corporation of Old Ridgebury Road, Danbury, Conn. 06817, United States of America).

Pump 26 was switched on in order to circulate liquid through the apparatus and autoclave 1 was heated to 88° C. under a total gas pressure of 195 psia (13.44 bar). The hydrogen partial pressure, the carbon monoxide partial pressure, and the nitrogen partial pressure were as in Comparative Example B.

When the apparatus had reached equilibrium; after about 3 hours from the start of the experiment, further n-nonanal was introduced into autoclave 1 by way of line 9 at a rate of 58 ml/hr, thus instigating $C_9$-aldehyde vaporisation in evaporator 24.

Approximately 9 hours after the start of the experiment, the n-nonanal feed was changed to a solution of approximately 3.0% v/v Filmer 351 in n-nonanal. This concentration was sufficient to ensure that the rate of removal of Filmer 351 by vaporisation in evaporator 24 balanced its rate of introduction, along with n-nonanal, by way of line 9. In this way a substantially constant liquid composition was achieved in autoclave 1 such that the n-nonanal concentration in the liquid medium was approximately 30%, corresponding to the aldehyde concentration at the end of Comparative Example B.

About 19 hours after the start of the experiment rhodium, in the form of $HRh(CO)(PPh_3)_3$, was charged to autoclave 1 so as to result in a rhodium concentration of 200 ppm w/v, calculated as rhodium metal. The feed to the reactor was then changed to 58 ml/hr of a 3% v/v solution of Filmer 351 in 1-octene.

The temperature of autoclave 1 was raised to 120° C. and hot oil was circulated through evaporator 24, also at 120° C.

In a manner similar to that described above in Comparative Example A, the composition of the reaction solution was determined. The results are plotted in FIG. 3.

Figure 3:
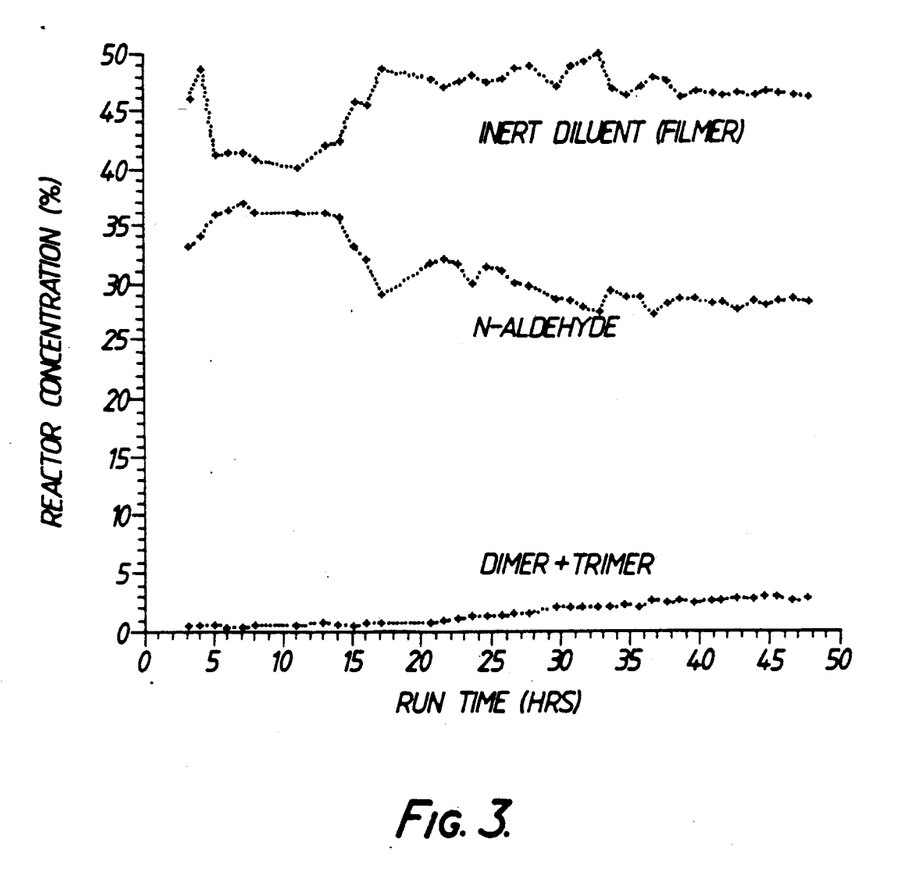

It will be seen that the rate of build up of "heavies", which are plotted in FIG. 3 as "DIMER+TRIMER" (i.e. a mixture of $C_{18}$ and $C_{29}$ aldehyde condensation products), is significantly lower in Example 2 than in Comparative Example B. Thus it will be possible to continue to operate the process for a considerably longer period of time, under the conditions of Example 2, than when using the conditions of Comparative Example B.

It will be appreciated by those skilled in the art that the conditions selected in Example 2 are more severe than the conditions preferred for industrial operation of the process, having been selected so as to be directly comparable with the conditions of Comparative Example B (which were in turn selected with the specific aim of causing a significant rate of formation of $C_{18}$ and higher "heavies" in the reaction solution such that the experiment would be completed within a reasonable time). Hence, in operating a commercial reactor, a temperature of, for example, about 105° C. could be used, thus resulting in a correspondingly lower rate of formation of $C_{18}$ and higher "heavies" than is indicated in FIG. 3. In this way the period for which a commercial reactor could be operated would be extended considerably beyond the length of time that could be achieved under conditions of Example 2 before the reaction had to be shut down either due to flooding of the reactor with "heavies" or to deactivation of the catalyst due to use of excessively high temperatures in evaporator 24.

We claim:

1. A continuous process for the production of aldehydes which contain from 7 to 17 carbon atoms and which are selected from unsubstituted aldehydes and aldehydes containing at least one substituent selected from ether groups and ester groups by hydroformylation of an olefin which contains from 6 to about 16 carbon atoms and which is selected from unsubstituted olefins and olefins containing at least one substituent selected from ether groups and ester groups to yield at least one product aldehyde containing one more carbon atom than said olefin, which process comprises:
   providing a hydroformylation zone, a product recovery zone, and means for circulating liquid between said hydroformylation zone and said product recovery zone;
   providing in said hydroformylation zone a substantially constant predetermined volume of a liquid hydroformylation medium containing uniformly distributed therein (a) a rhodium complex hydroformylation catalyst comprising rhodium in complex combination with carbon monoxide and with a ligand, (b) free ligand, (c) not more than a predetermined minor amount of at least one said aldehyde, and (d) an inert solvent that is less volatile than any aldehyde formed by the hydroformylation reaction but is more volatile than said ligand;
   continuously supplying carbon monoxide and hydrogen to said hydroformylation zone;
   continuously supplying said olefin to said hydroformylation zone;
   maintaining said hydroformylation zone under temperature and pressure conditions effective for causing hydroformylation of said olefin in the presence of said rhodium complex hydroformylation catalyst;
   passing liquid hydroformylation medium to said product recovery zone;
   maintaining said product recovery zone under vaporization conditions selected to cause vaporization of said at least one optionally substituted aldehyde and at least a minor amount of said solvent;
   recovering from said product recovery zone (i) a vaporous stream containing a major amount of said at least one aldehyde and a minor amount of said solvent and (ii) a liquid stream containing said catalyst and said ligand;
   continuously recycling said liquid stream to said hydroformylation zone;
   controlling the vaporization conditions in the product recovery zone so that the rate at which said solvent is recovered in said vaporous stream is at least equal to the rate of formation of aldehyde condensation by-products in said hydroformylation zone; and
   controlling the volume of liquid in said hydroformylation zone by supplying solvent thereto, at a rate sufficient to maintain said substantially constant predetermined volume of liquid hydroformylation medium in said hydroformylation zone;
   whereby the amount of said at least one aldehyde in said hydroformylation zone is maintained at or below said predetermined minor amount so as to minimize the rate of formation of aldehyde condensation by-products and whereby said solvent is gradually displaced from the hydroformylation zone by high boiling materials including aldehyde condensation by-products formed by self-condensation of said at least one aldehyde.

2. A process according to claim 1, in which the olefin contains from 8 to 16 carbon atoms.

3. A process according to claim 1, in which the olefin is selected from 1-hexene, cis- and trans-2- and -3-hexene, 1-heptene, cis- and trans-2-, and -3-heptene, 1-octene, cis- and trans-2-, -3-, and -4-octene, 1-nonene, cis- and trans-2-nonene, 1-decene, cis- and trans-2-decene, 1-undecene, 1-dodecene, 1-tridecene, 1-tetradecene, 1-hexadecene, 1-octadecene, 2-, 3-, 4- and 5-methyl-1-hexene, 2-methyl-1-heptene, 2-methyl-2-heptene, 2-, 3-, and 4-methyl-1-pentene, 2-methyl-2-pentene, cis- and trans-3-methyl-2-penetene, 2-methyl-1- and -2-heptene, allyl t-butyl ether, allyl propionate, allyl n-butyrate, and allyl caproate.

4. A process according to claim 1, in which the olefin contains one or more alpha-olefinic groups of the formula $-CH:CH_2$ or $>C:CH_2$ and the ligand is a triarylphosphine.

5. A process according to claim 4, in which the triarylphosphine is triphenylphosphine.

6. A process according to claim 1, in which the olefin contains one or more internal olefinic groups of the formula >C:C< and the ligand is a triarylphosphite or a cyclic phosphite.

7. A process according to claim 1, in which the hydroformylation medium contains from about 20 ppm up to about 500 ppm rhodium, calculated as rhodium metal, and at least one mole of free ligand per mole of rhodium catalyst.

8. A process according to claim 1, in which the concentration of ligand in the hydroformylation medium ranges from about 5% by volume up to about 20% by volume.

9. A process according to claim 1, in which the inert solvent is selected so as to have a boiling point at the pressure prevailing in the product recovery zone that is at least about 10° C. higher than that of aldehyde hydroformylation product at that pressure.

10. A process according to claim 9, in which the boiling point of the solvent at the pressure prevailing in the product recovery zone is at least about 10° C. lower than that of the ligand at that pressure.

11. A process according to any claim 1, in which the solvent is selected from hydrocarbons, ethers, ketones, and materials derived from the product aldehydes.

12. A process according to claim 1, in which the inert solvent comprises a mixture of aldehyde condensation products formed as by-products of the hydroformylation of a $C_2$ to $C_5$ olefin.

13. A process according to claim 1, in which the rate of recovery of the liquid hydroformylation medium from the hydroformylation zone and the rate of recycle of catalyst containing solution and, the rate of supply of solvent to the hydroformylation zone are so selected as to maintain in the hydroformylation zone a product aldehyde concentration of from about 1 to about 2 gram moles of product aldehyde per liter of reaction medium.

14. A process according to claim 1, in which the hydroformylation conditions include use of a temperature in the range of from about 40° C. to about 160° C. and a pressure in the range of from about 1 bar absolute up to about 100 bar absolute.

15. A process according to claim 1, in which the product recovery zone is operated at a temperature in the range of from about 60° C. up to about 160° C., at a pressure of from about 0.0001 bar absolute up to about 0.5 bar absolute, and with a residence time in the range of from about 5 seconds to about 2 minutes.

16. A process according to claim 1, in which the product recovery zone comprises a distillation column, a wiped film evaporator, or a falling film evaporator.

17. A process according to claim 1, in which the solvent recovery zone follows immediately after the product recovery zone.

18. A process according to claim 17, in which the recovery zone comprises a fractionation zone, from which the product aldehydes are recovered overhead, together with unreacted olefin or olefins and hydrogenation by-products, and from which the solvent is recovered as a bottom product.

19. A process according to claim 1 wherein said hydroformylation conditions comprise a temperature of about 40° C. to about 160° C. and a pressure of about 1 bar absolute to about 100 bar absolute.

* * * * *

UNITED STATES PATENT AND TRADEMARK OFFICE
CERTIFICATE OF CORRECTION

PATENT NO. : 5,053,551

DATED : October 1, 1991

INVENTOR(S) : George Edwin Harrison et al.

It is certified that error appears in the above-identified patent and that said Letters Patent is hereby corrected as shown below:

Column 6, line 65, "2-, methyl-" should be --2-methyl---.

Column 9, line 35, "zene" and "di-n-octyl ether" should be on separate lines.

Column 12, line 68, "produce" should be --product--.

Column 13, line 57, "liters hour" should be --litres/hour--.

Column 16, line 58, "equilibrium;" should be --equilibrium,--.

Column 19, first line of claim 11, delete "any".

Signed and Sealed this

Twenty-second Day of June, 1993

Attest:

MICHAEL K. KIRK

*Attesting Officer*  *Acting Commissioner of Patents and Trademarks*